US011752068B2

(12) United States Patent
Liscio (10) Patent No.: US 11,752,068 B2
(45) Date of Patent: Sep. 12, 2023

(54) MEDICAMENT CONTAINER AND DRUG DELIVERY DEVICE

(71) Applicant: SANOFI, Paris (FR)

(72) Inventor: Edward Liscio, Bridgewater, NJ (US)

(73) Assignee: Sanofi, Paris (FR)

( * ) Notice: Subject to any disclaimer, the term of this patent is extended or adjusted under 35 U.S.C. 154(b) by 198 days.

(21) Appl. No.: 16/755,964

(22) PCT Filed: Sep. 26, 2018

(86) PCT No.: PCT/EP2018/076048
§ 371 (c)(1),
(2) Date: Apr. 14, 2020

(87) PCT Pub. No.: WO2019/076593
PCT Pub. Date: Apr. 25, 2019

(65) Prior Publication Data
US 2020/0297580 A1    Sep. 24, 2020

(30) Foreign Application Priority Data
Oct. 19, 2017 (EP) .................... 17306418

(51) Int. Cl.
*A61J 1/10* (2006.01)
*A61J 1/14* (2023.01)
(Continued)

(52) U.S. Cl.
CPC .............. *A61J 1/10* (2013.01); *A61J 1/1406* (2013.01); *A61J 1/2013* (2015.05); *A61M 2005/206* (2013.01)

(58) Field of Classification Search
CPC .......... A61J 1/10; A61J 1/1406; A61J 1/2013; A61J 1/14; A61J 1/1462; A61J 1/201;
(Continued)

(56) References Cited

U.S. PATENT DOCUMENTS

| 1,522,198 A | * | 1/1925 | Marcy | ............... A61M 5/282 |
| | | | | 604/243 |
| 2,798,488 A | * | 7/1957 | Hall | .................. A61M 3/00 |
| | | | | 604/82 |

(Continued)

FOREIGN PATENT DOCUMENTS

| CN | 1250383 | 4/2000 |
| CN | 102271735 | 12/2011 |

(Continued)

OTHER PUBLICATIONS

Otsu, Okayama, Ogawa, Prefilled Syringe, Oct. 27, 2011, machine translation (Year: 2011).*

(Continued)

*Primary Examiner* — Andrew J Mensh
*Assistant Examiner* — Brandon W. Levy
(74) *Attorney, Agent, or Firm* — Fish & Richardson P.C.

(57) ABSTRACT

The present disclosure relates to a medicament container, configured as a flexible bag. The flexible bag includes a proximal end and a distal end having an outlet port. The flexible bag is configured to increase in length between the proximal end and the distal end when being collapsed.

18 Claims, 3 Drawing Sheets

(51) Int. Cl.
*A61J 1/20* (2006.01)
*A61M 5/20* (2006.01)

(58) Field of Classification Search
CPC ............ A61J 1/1475; A61J 1/067; A61J 1/00;
A61M 2005/206; A61M 5/20; A61M
5/3243; A61M 5/2466; A61M 5/2425;
A61M 2005/2411; A61M 2005/247;
A61M 2005/3247; A61M 5/282; A61M
15/0028; A61M 5/145; A61M 37/00;
A61M 11/006; A61M 5/148; A61M
5/3287; A61M 2005/005; A61M 5/2459;
G16H 20/17; B05B 11/02; B05B 11/04
See application file for complete search history.

(56) References Cited

U.S. PATENT DOCUMENTS

| | | | |
|---|---|---|---|
| 5,328,483 A | 7/1994 | Jacoby | |
| 5,354,286 A * | 10/1994 | Mesa | A61M 5/2033 |
| | | | 604/218 |
| 2004/0015121 A1 | 1/2004 | Ryan et al. | |
| 2006/0084926 A1 | 4/2006 | Fitzgerald | |
| 2007/0191780 A1 * | 8/2007 | Modi | A61M 5/286 |
| | | | 604/187 |
| 2010/0137808 A1 | 6/2010 | Wilmot et al. | |
| 2010/0179473 A1 | 7/2010 | Genosar | |
| 2010/0249728 A1 * | 9/2010 | Kobashi | A61J 1/10 |
| | | | 604/262 |
| 2012/0197212 A1 | 8/2012 | Basso et al. | |
| 2012/0266875 A1 | 10/2012 | Nagel et al. | |
| 2013/0006216 A1 | 1/2013 | Taylor et al. | |
| 2013/0110053 A1 * | 5/2013 | Yoshino | A61M 5/2425 |
| | | | 604/414 |
| 2015/0112263 A1 | 4/2015 | Tremblay et al. | |
| 2016/0058960 A1 * | 3/2016 | Papania | A61M 15/0028 |
| | | | 128/200.22 |

FOREIGN PATENT DOCUMENTS

| | | | | |
|---|---|---|---|---|
| CN | 102481413 | | 5/2012 | |
| JP | 2011212184 A | * | 10/2011 | ............ A61M 5/282 |
| JP | 2013-502952 | | 1/2013 | |
| JP | 2013-543759 | | 12/2013 | |
| WO | WO 1998/031409 | | 7/1998 | |
| WO | WO 2010/068415 | | 6/2010 | |
| WO | WO 2011/023632 | | 3/2011 | |

OTHER PUBLICATIONS

International Preliminary Report on Patentability in Application No. PCT/EP2018/076048, dated Apr. 21, 2020, 6 pages.
International Search Report and Written Opinion in Application No. PCT/EP2018/076048, dated Oct. 26, 2018, 10 pages.

* cited by examiner

MEDICAMENT CONTAINER AND DRUG DELIVERY DEVICE

CROSS REFERENCE TO RELATED APPLICATIONS

The present application is the national stage entry of International Patent Application No. PCT/EP2018/076048, filed on Sep. 26, 2018, and claims priority to Application No. EP 17306418.9, filed on Oct. 19, 2017, the disclosures of which are incorporated herein by reference.

TECHNICAL FIELD

The disclosure generally relates to a medicament container, including a bag with an outlet, the bag compressible by a compression means. In particular, the disclosure relates to a drug delivery device adapted to receive a medicament container configured as a flexible bag.

BACKGROUND

Many medicaments have to be injected into the body. This applies in particular to medicaments, which are deactivated or have their efficiency remarkably decreased by oral administration, e.g. proteins (such as insulin, growth hormones, and interferons), carbohydrates (e.g. heparin), antibodies and the majority of vaccines. Such medicaments are predominantly injected by means of medicament containers, typically glass or plastic syringes or cartridges.

There is a need for improved medicament containers that are simple and reliable in use

SUMMARY

An aspect of the present disclosure is to provide an improved medicament container and an improved drug delivery device.

According to an aspect of the present disclosure a medicament container is configured as a flexible bag comprising a proximal end and a distal end having an outlet port, wherein the flexible bag is configured to increase in length between the proximal end and the distal end when being collapsed.

In an example of an embodiment, the outlet port comprises a membrane adapted to be pierced by a hollow tube, e.g. a hollow needle.

In an example of an embodiment, the proximal end of the medicament container comprises a flat section, i.e. a section where two opposing walls of the bag are in contact with each other so that there is no medicament or almost no medicament between these two opposing walls in this flat section.

In an example of an embodiment, the flat section comprises one or more holes for fixing the proximal end of the container.

In an example of an embodiment, at least two holes are provided, each hole having one out of at least two different shapes so that a sequence of the shapes of the holes forms an identifier for the container and/or for the medicament contained in the container.

In an example of an embodiment, the container has a profile which decreases towards the proximal end and/or the distal end of the container.

In an example of an embodiment, an inside of the medicament container exhibits a coating to prevent the medicament from extracting or leaching a material of the container.

In an example of an embodiment, the container is configured as a bag comprising a flexible material, e.g. a plastic, aluminium, polyethylene, a thermoplastic elastomer (TPE), PVC (Polyvinyl Chloride), PVC/NBR (PVC Nitrile), TPE-MPR (thermoplastic elastomer-melt processable rubber), TPE-Vinyl-based, TPE (Thermoplastic vulcanizate, also known as Santoprene®), POP (Polyolefin plastomer), Tee (Thermoplastic polyester co-polymer).

In an example of an embodiment, the medicament container is formed by impact extrusion or by injection molding or blow molding In an example of an embodiment, the flat section is formed by folding the initially open proximal end or by bonding, in particular ultrasonic welding or gluing In an example of an embodiment, the medicament container contains a medicament.

According to an aspect of the present disclosure, a drug delivery device comprises a housing adapted to receive a medicament container as described above, a squeezer adapted to collapse the medicament container when driven by a drive mechanism, a dual tip injection needle fixed within the housing, wherein in an initial state before the medicament container is collapsed a proximal tip of the needle is spaced from the membrane. As the container increase in length when being collapsed by the squeezer, the proximal tip of the needle pierces the membrane as the container is being collapsed. Thus, the container is maintained sterile until being collapsed.

In an example of an embodiment, the squeezer comprises at least one roller adapted to collapse the medicament container when being moved in a distal direction while a proximal end of the container remains in position within the housing such that the membrane is moved towards the proximal tip as the flexible bag increases in length between the proximal end and the distal end when being collapsed so that the proximal tip pierces the membrane.

In an example of an embodiment, the squeezer comprises two rollers adapted to collapse the medicament container between them when being moved in the distal direction. Two rollers may provide better volume delivery accuracy than one roller because the two rollers will squeeze the entire medicament out of the container even under high pressure. A single roller may allow for fluid leakage past the single roller under pressure so medicament may be trapped behind the roller as it advances in the distal direction.

In an example of an embodiment, the housing comprises roller tracks to guide the at least one roller during movement in the distal direction.

In an example of an embodiment, the drug delivery device comprises a medicament container as described above and containing a medicament.

The drug delivery device may be an auto-injector wherein the drive mechanism could be operated by a mechanical or gas spring or by an electric motor. In other embodiments, the drug delivery device may be a pen-type device wherein the drive mechanism would be manually operated.

The drug delivery device, as described herein, may be configured to inject a drug or medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector.

The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device. The one or more automated functions of an auto-injector may be activated via an activation mechanism. Such an activation mechanism can include one or more of a button, a lever, a needle sleeve, or other activation component. Activation may be a one-step or multi-step process. That is, a user may need to activate one or more activation mechanism in order to cause the automated function. For example, a user may depress a needle sleeve against their body in order to cause injection of a medicament. In other devices, a user may be required to depress a button and retract a needle shield in order to cause injection. In other devices, a user may be required to place the device against the skin and the device with sensor would activate automatically with a small time delay.

In addition, such activation may activate one or more mechanisms. For example, an activation sequence may activate at least two of needle insertion, medicament injection, and needle retraction. Some devices may also require a specific sequence of steps to cause the one or more automated functions to occur. Other devices may operate with sequence independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Further scope of applicability of the present disclosure will become apparent from the detailed description given hereinafter. However, it should be understood that the detailed description and specific examples, while indicating example embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become more fully understood from the detailed description given below and the accompanying drawings, which are given by way of illustration only, and do not limit the present disclosure, and wherein.

Corresponding parts are marked with the same reference symbols in all figures.

DETAILED DESCRIPTION

Figure 1A:
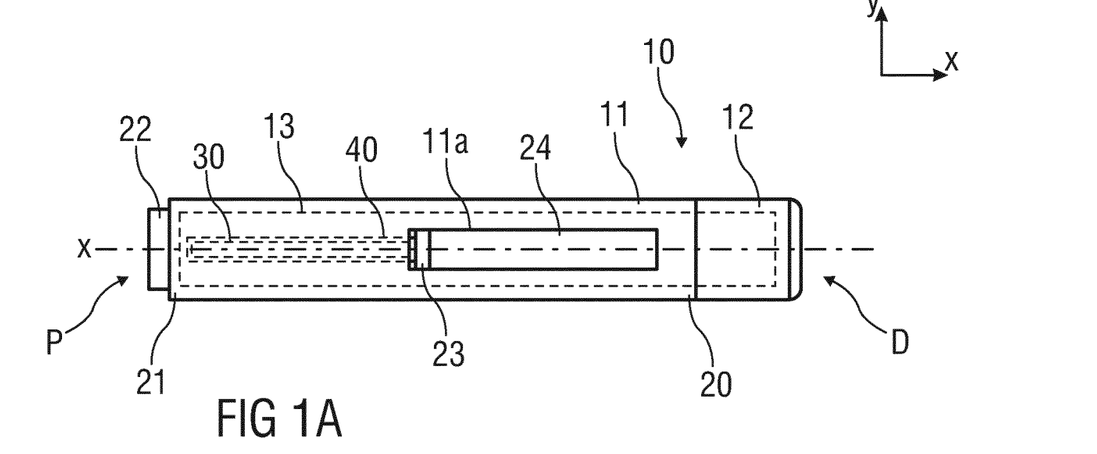
FIG. 1 is a schematic view of a drug delivery device.
Figure 1B:
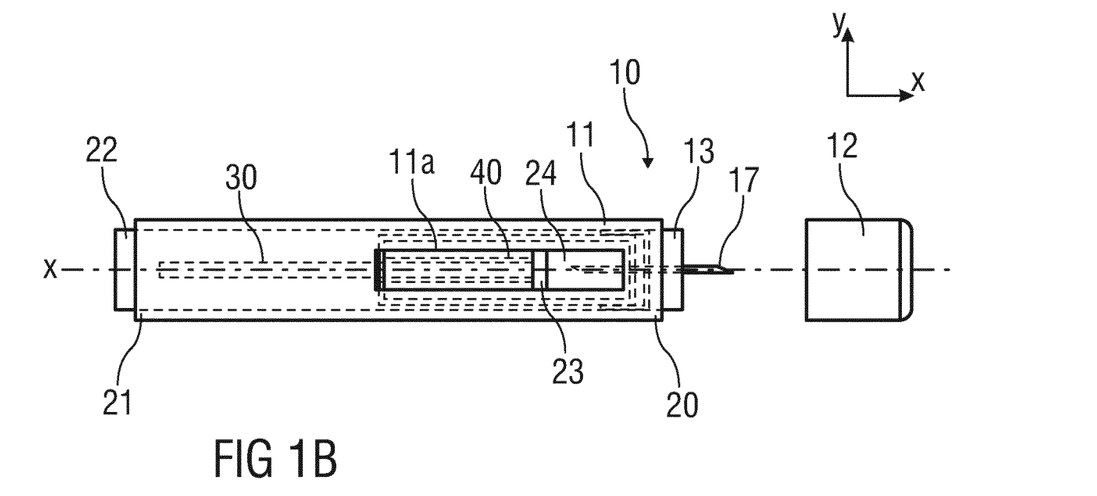

According to some embodiments of the present disclosure, an example of a drug delivery device 10 is shown in FIGS. 1A and 1B.

Device 10, as described above, is configured to inject a drug or medicament into a patient's body.

Device 10 includes a housing 11 which typically contains a reservoir containing the medicament to be injected (e.g., a syringe or a container 24) and the components required to facilitate one or more steps of the delivery process.

Device 10 can also include a cap assembly 12 that can be detachably mounted to the housing 11, in particular on a distal or front end D of the device 10. Typically, a user must remove cap assembly or cap 12 from housing 11 before device 10 can be operated.

As shown, housing 11 may be substantially cylindrical and have a substantially constant diameter along the longitudinal axis X. The housing 11 may have a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to the housing 11 to permit movement of the sleeve 13 relative to the housing 11. For example, the sleeve 13 can move in a longitudinal direction parallel to longitudinal axis X. Specifically, movement of the sleeve 13 in a proximal direction can permit a tube or needle 17 to extend from distal region 20 of housing 11. Insertion of the needle 17 can occur via several mechanisms. For example, the needle 17 may be fixedly located relative to housing 11 and initially be located within an extended needle sleeve 13. Proximal movement of the sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as the needle 17 is manually inserted via the patient's manual movement of the housing 11 relative to the sleeve 13.

Another form of insertion is "automated," whereby the needle 17 moves relative to housing 11. Such insertion can be triggered by movement of sleeve 13 or by another form of activation, such as, for example, a button 22. As shown in FIGS. 1A & 1B, button 22 is located at a proximal or back end P of the housing 11. However, in other embodiments, button 22 could be located on a side of housing 11. In further embodiments, the button 22 has been deleted and is replaced for instance by a sleeve trigger mechanism, e.g. provided by pushing the needle sleeve 13 inside the housing when the drug delivery device is put onto an injection side.

Other manual or automated features can include drug injection or needle retraction, or both.

Following injection, the needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of the sleeve 13 has moved past a distal end of the needle 17, and the needle 17 is covered, the sleeve 13 can be locked. Such locking can include locking any proximal movement of the sleeve 13 relative to the housing 11.

Another form of needle retraction can occur if the needle 17 is moved relative to the housing 11. Such movement can occur if the syringe within the housing 11 is moved in a proximal direction relative to the housing 11. This proximal movement can be achieved by using a retraction spring (not shown), located in the distal region 20. A compressed retraction spring, when activated, can supply sufficient force to the container 24 to move it in a proximal direction. Following sufficient retraction, any relative movement between the needle 17 and the housing 11 can be locked with a locking mechanism. In addition, button 22 or other components of device 10 can be locked as required.

In some embodiments, the housing may comprise a window 11a through which the container 24 can be monitored.

Figure 2:
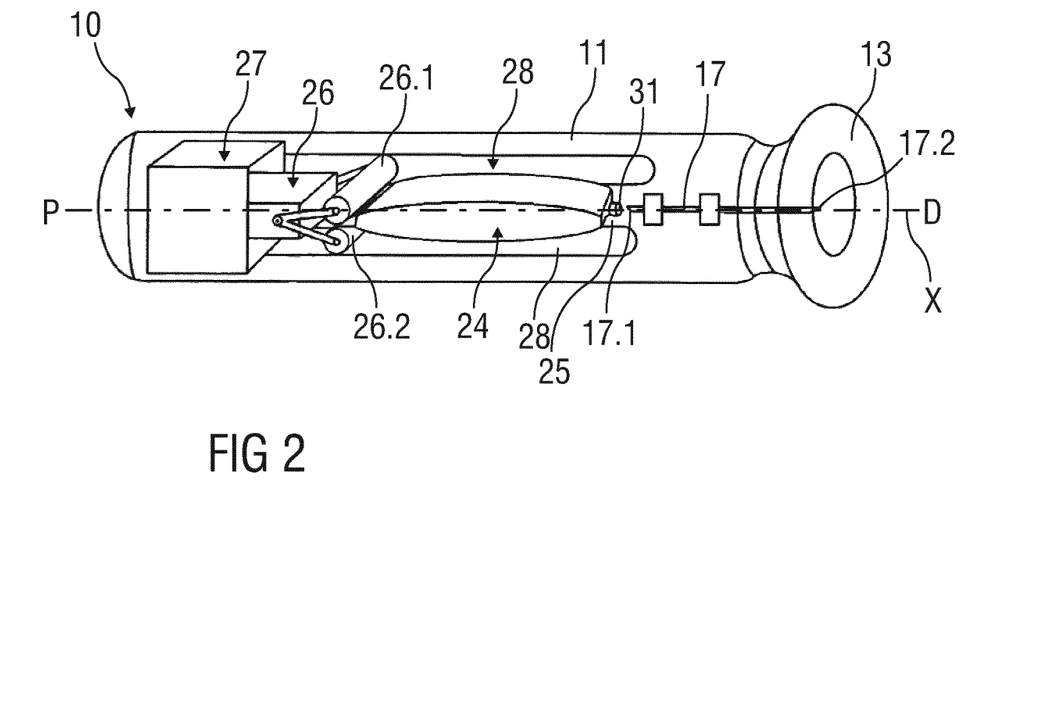
FIG. 2 is a schematic view of an example of an embodiment of a drug delivery device prior to delivery of a drug.

FIG. 2 is a schematic view of an example of an embodiment of a drug delivery device 10 prior to delivery of a drug. The drug delivery device 10 comprises a container 24 filled with the drug, the container 24 configured as a flexible bag having an outlet port 25. The container 24, preferably having a relatively thin skin, is compressible by a squeezer 26 comprising a pair of rollers 26.1, 26.2 movable in parallel with the longitudinal axis X by a drive mechanism 27. The container 24 is arranged between the rollers 26.1, 26.2 so as to be collapsed when the rollers 26.1, 26.2 are moved along the longitudinal axis X in a distal direction D while a proximal end of the container 24 remains in position within the housing 11. Due to the rollers 26.1, 26.2 collapsing the container 24 a volume of the container 24 are gradually reduced and consequently the drug is squeezed out of the outlet port 25. In an example of an embodiment, the housing 11 comprises roller tracks 28 adapted to guide the rollers 26.1, 26.2 and to maintain a distance between the two rollers 26.1, 26.2 as they are advanced.

The rollers 26.1, 26.2 may be spaced from each other such that, taking into account a wall thickness of the container 24, the container 24 is completely collapsed so that no medicament becomes trapped behind the rollers 26.1, 26.2 as they are moved.

The container 24 may be configured as a plastic blow molded bag or as an aluminium bag. The outlet port 25 is arranged on a distal end of the container 24, e.g. by molding. The outlet port 25 may comprise a thin-walled membrane 31 adapted to be pierced by a proximal tip 17.1 of a dual tip injection needle 17 which is fixed within the housing 11. A distal tip 17.2 of the needle 17 may be positioned to distally extend from the housing 11 after removal of a cap assembly (not shown) or after depression of the sleeve 13. In an initial state prior to an injection, the proximal tip 17.1 of the needle 17 is spaced from the membrane 31 of the outlet port 25 so that the contents of the container 24 are maintained sterile and container integrity. A proximal end of the container 24 comprises a flat section 29 (cf. FIG. 3) adapted to be fixed within the housing 11. As the rollers 26.1, 26.2 are being advanced in the distal direction D, the flat section 29 remains in position within the housing 11 held by one or more holes 30 while the container 24 is gradually collapsed and therefore increases in length so that the outlet port 25 moves toward the proximal tip 17.1 of the needle 17 until the proximal tip 17.1 pierces the membrane 31 thus establishing a fluid communication between the container 24 and the needle 17.

In an example of an embodiment, the container 24 shaped as a bag may have a circular, elliptical or rectangular profile. In an example of an embodiment, the profile is not uniform but decreases towards the proximal and distal end of the container 24 or at least towards the distal end or the proximal end.

Figure 3:
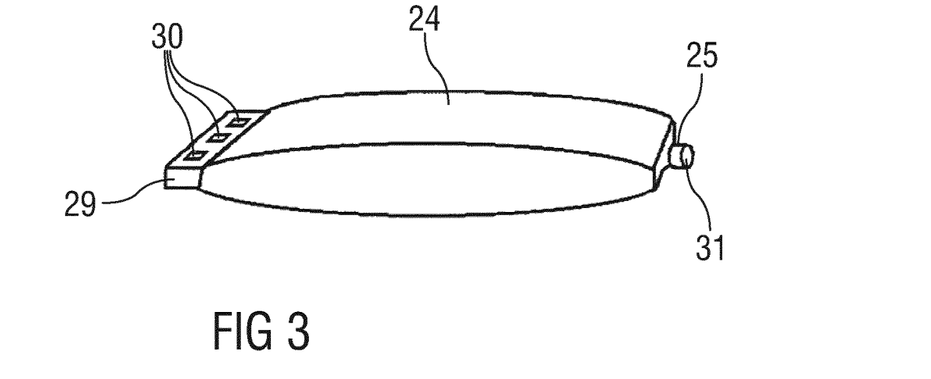
FIG. 3 is a schematic view of the bag.

In the case of an aluminium bag, the bag may be formed by impact extrusion, wherein the bag is extruded from a small piece of aluminium. The flat section 29 may be formed by folding the initially open proximal end several times as with a tube of tooth paste. The bag is thus hermetically sealed and nearly germ-free due to high temperatures during the production process of the bag. An inside of the bag may exhibit a coating to prevent the material of the bag from reacting with the contents.

In the case of a plastic bag, the flat section 29 may be formed by bonding, e.g. by applying an adhesive or by welding. The flat section 29 is shown in FIG. 3.

In the case of a plastic bag the outlet port 25 may be formed by injection molding of a preform to form the membrane 31. The preform may be formed as a miniature version of the bag, e.g. comprising a neck having the final shape and size of the outlet port 25, optionally with threads and with a small, thick-walled section for forming the body part of the bag which will subsequently be blown into the final shape. The preform may be loaded into a molding press, heated and pressurized in a blow molding tool. Compressed air may be used to form it to the shape of the blow molding tool forming the final shape. Because the neck and threads are injection molded when the preform is made, they are produced very accurately, enabling an excellent seal with the cap, also referred to as the closure which is injection mold. Thus, no insert or liner is required inside the closure to produce an excellent leak-proof seal.

The flat section 29 may comprise one or more holes 30 which may be used to fix the container 24 within the housing 11. The housing 11 or the drive mechanism 27 may have pins adapted to engage in the holes 30. The holes 30 may have different shapes, e.g. star or asterisk, square, circle, diamond, triangle etc. A sequence of holes 30, each one having one of these shapes, can be used to form a unique identifier for the container 24 and/or for the medicament contained in the container 24. In case of three holes 30 there can be eight different identifiers using two different symbols. Using three different symbols there would be 27 different identifiers; using four different symbols there would be 64 different identifiers etc.

Figure 4:
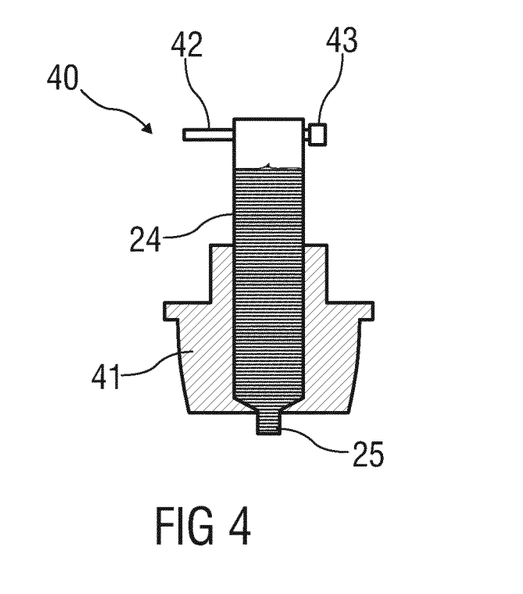
FIG. 4 is a schematic view of an ultrasonic sealer.

The container 24 may consist of or comprise a plastic material, e.g. polyethylene. FIG. 4 is a schematic view of an ultrasonic sealer 40 comprising a container holder 41 for receiving a container 24 with the outlet port 25 down. The container 24 is filled with a drug, e.g. from bottom up. An ultrasonic horn 42 and a fixture 43 are arranged at the proximal end of the container 24 for closing and sealing the proximal end and forming the flat section 29 by ultrasonic welding. In other embodiments, the proximal end of the container 24 could be sealed by heat or in a different way. The sealing may occur in a clean-room.

Figure 5:
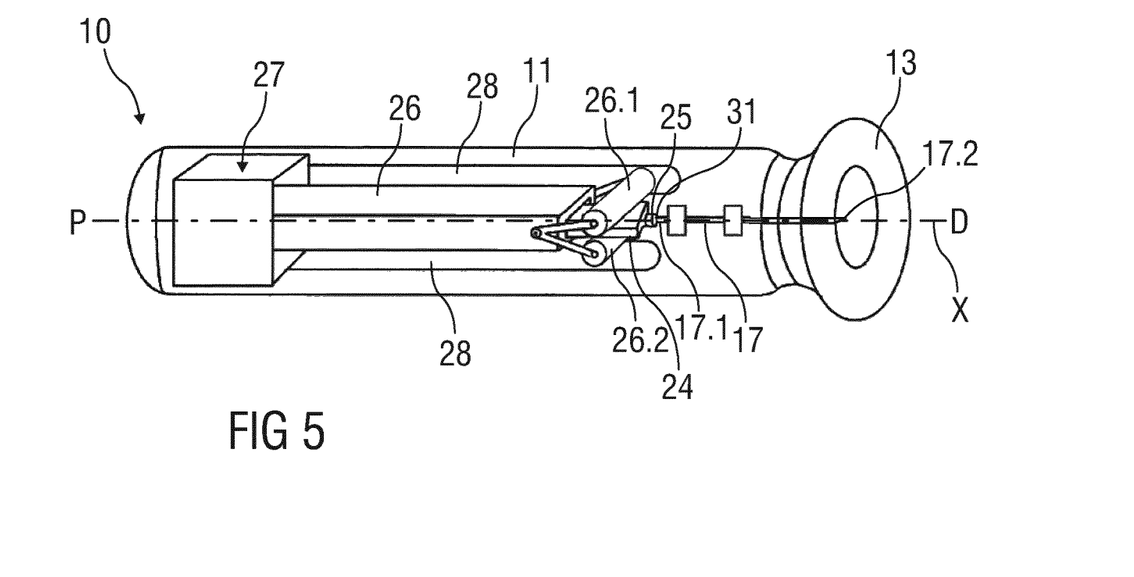
FIG. 5 is a schematic view of the drug delivery device after delivery of a drug.

FIG. 5 is a schematic view of the drug delivery device 10 after delivery of a drug. The drive mechanism 27 has advanced the rollers 26.1, 26.2 in the distal direction D, wherein the flat section 29 remained in position while the container 24 was gradually collapsed and therefore increased in length so that the outlet port 25 moved toward the proximal tip 17.1 of the needle 17 and the proximal tip 17.1 pierced the membrane 31 thus establishing a fluid communication between the container 24 and the needle 17. Due to the rollers 26.1, 26.2 collapsing the container 24 a volume of the container 24 were gradually reduced and consequently the drug was squeezed out of the outlet port 25 through the needle 17. After drug delivery, the cap assembly may be put back on the housing 11 to cover the distal tip 17.2 of the needle 17.

The drug delivery device 10 may be an auto-injector wherein the drive mechanism could be operated by a mechanical or gas spring or by an electric motor. In other embodiments, the drug delivery device 10 may be a pen-type device wherein the drive mechanism would be manually operated.

In another example of an embodiment, instead of the rollers 26.1, 26.2, the squeezer 26 could be arranged as an axle engaging the proximal end of the container 24 to coil it up as the axle is rotated.

In yet another embodiment, the squeezer 26 could comprise only one roller 26.1 acting against a rigid support on which the container 24 would be placed.

In another example of an embodiment, a needle connected to tubing could be arranged instead of the dual tip needle, the other end of the tubing being connected to another needle or cannula.

In an example of an embodiment, the membrane 31 may be a septum, e.g. a pizza-shaped septum, adapted to reseal the container 24.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Examples of pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Examples of disorders include, but are not limited to, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis.

Examples of drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Examples of insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034, MOD-6030, CAM-2036, DA-15864, ARI-2651, ARI-2255, Exenatide-XTEN and Glucagon-Xten.

An example of a oligonucleotide is, for example: mipomersen/Kynamro, a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 10 drug delivery device
11 housing
11a window
12 cap assembly
13 sleeve
17 needle
17.1 proximal tip
17.2 distal tip
20 distal region
21 proximal region 22 button
24 container
25 outlet port
26 squeezer
26.1 roller
26.2 roller
27 drive mechanism
28 roller track
29 flat section
30 hole
31 membrane
40 ultrasonic sealer
41 container holder
42 ultrasonic horn
43 fixture
D distal end, distal direction
P proximal end, proximal direction
X longitudinal axis

The invention claimed is:

1. A medicament container comprising:
    a flexible bag comprising a proximal end and a distal end, the distal end comprising an outlet port, wherein the outlet port comprises a membrane adapted to be pierced by a hollow tube or a needle and wherein the outlet port is moved towards the hollow tube or the needle as the flexible bag increases in length between the proximal end and the distal end during a transition of the flexible bag to a collapsed state;
    wherein the length between the proximal end and the distal end of the flexible bag is greater after the transition to the collapsed state than before the transition to the collapsed state,
    wherein a distance between the proximal end of the flexible bag and the hollow tube or the needle remains unchanged before, during and after transition of the flexible bag to the collapsed state, and
    wherein in the collapsed state a volume of the flexible bag is less than before the transition to the collapsed state.

2. The medicament container of claim 1, wherein the flexible bag has a profile which decreases towards at least one of the proximal end and the distal end of the flexible bag.

3. The medicament container of claim 1, wherein the proximal end of the flexible bag comprises a flat section.

4. The medicament container of claim 3, wherein the flat section comprises one or more holes.

5. The medicament container of claim 4, wherein the flat section comprises at least two holes having at least two different shapes, wherein a sequence of the at least two different shapes forms an identifier.

6. The medicament container of claim 3, wherein the flat section is formed by folding the initially open proximal end or by bonding, wherein bonding comprises ultrasonic welding.

7. The medicament container of claim 1, wherein an inside of the medicament container comprises a coating to prevent a material of the flexible bag from reacting with a medicament.

8. The medicament container of claim 1, wherein the flexible bag is configured as a bag comprising a flexible material.

9. The medicament container of claim 8, wherein the flexible material comprises one of a plastic, aluminium, polyethylene, a thermoplastic elastomer, polyvinyl chloride, polyvinyl chloride Nitrile, melt processable rubber based thermoplastic elastomer, Vinyl-based thermoplastic elastomer, thermoplastic vulcanizate, polyolefin plastomer and thermoplastic polyester co-polymer.

10. The medicament container of claim 8, wherein the flexible bag is formed by impact extrusion, or by at least one of injection molding and blow molding.

11. The medicament container of claim 1, containing a medicament.

12. A drug delivery device comprising
    a housing adapted to receive a medicament container, the medicament container comprising a flexible bag, the flexible bag comprising a proximal end and a distal end, the distal end comprising an outlet port, wherein the flexible bag is configured to increase in length between the proximal end and the distal end during a transition of the flexible bag to a collapsed state, wherein the length between the proximal end and the distal end of the flexible bag is greater after the transition to the collapsed state than before the transition to the collapsed state, wherein a distance between the proximal end of the flexible bag and the hollow tube or the needle remains unchanged before, during and after transition of the flexible bag to the collapsed state, wherein in the collapsed state a volume of the flexible bag is less than before the transition to the collapsed state, wherein the outlet port comprises a membrane adapted to be pierced by a needle as the flexible bag increases in length;
    a squeezer comprising a roller, the squeezer adapted to collapse the medicament container in response to being driven by a driving component; and
    a dual tip injection needle fixed within the housing, wherein in an initial state before the medicament container is collapsed a proximal tip of the needle is spaced from the outlet port;
    wherein the driving component is operated by a mechanical or gas spring or by an electrical motor.

13. The drug delivery device of claim 12, wherein the roller is adapted to collapse the medicament container when the squeezer is moved in a distal direction and the proximal end of the medicament container remains in position within the housing such that the membrane is moved towards the proximal tip of the needle as the flexible bag increases in length between the proximal end and the distal end when the medicament container is being collapsed so that the proximal tip of the needle pierces the membrane.

14. The drug delivery device of claim 13, wherein the squeezer comprises a second roller, the roller and second roller being adapted to collapse the medicament container between the roller and second roller in response to the squeezer being moved in the distal direction.

15. The drug delivery device of claim 13, wherein the housing comprises roller tracks to guide the roller during movement in the distal direction.

16. A drug delivery device comprising:
    a medicament container, the medicament container containing a medicament and comprising a flexible bag, the flexible bag comprising a proximal end and a distal end, the distal end comprising an outlet port, wherein the outlet port comprises a membrane adapted to be pierced by a hollow tube or a needle and wherein the outlet port is moved towards the hollow tube or the needle as the flexible bag increases in length between the proximal end and the distal end during a transition of the flexible bag to a collapsed state, wherein the length between the proximal end and the distal end of the flexible bag is greater after the transition to the collapsed state than before the transition to the collapsed state, wherein a distance between the proximal end of the flexible bag and the hollow tube or the needle remains unchanged before, during and after transition of the flexible bag to the collapsed state, and wherein in the collapsed state a volume of the flexible bag is less than before the transition to the collapsed state.

17. The drug delivery device of claim 16, wherein the flexible bag has a profile which decreases towards at least one of the proximal end and the distal end of the flexible bag.

18. The drug delivery device of claim 16, wherein the proximal end of the flexible bag comprises a flat section, the flat section comprising one or more holes.

\* \* \* \* \*